US012565633B2

(12) United States Patent
Han et al.

(10) Patent No.: US 12,565,633 B2
(45) Date of Patent: Mar. 3, 2026

(54) CELL CULTURE DEVICE

(71) Applicant: AMOGREENTECH CO., LTD.,
Gimpo-si (KR)

(72) Inventors: Kyoung Ku Han, Gimpo-si (KR); Seon Ho Jang, Gimpo-si (KR); Jae Kyung Song, Gimpo-si (KR); Hee Sung Park, Gimpo-si (KR)

(73) Assignee: AMOGREENTECH CO., LTD.,
Gimpo-si (KR)

( * ) Notice: Subject to any disclaimer, the term of this patent is extended or adjusted under 35 U.S.C. 154(b) by 665 days.

(21) Appl. No.: 18/000,696

(22) PCT Filed: May 28, 2021

(86) PCT No.: PCT/KR2021/006668
§ 371 (c)(1),
(2) Date: Feb. 8, 2023

(87) PCT Pub. No.: WO2021/246726
PCT Pub. Date: Dec. 9, 2021

(65) Prior Publication Data
US 2023/0174910 A1     Jun. 8, 2023

(30) Foreign Application Priority Data

Jun. 5, 2020     (KR) ........................ 10-2020-0068450

(51) Int. Cl.
*C12M 1/32*          (2006.01)
*C12M 1/12*          (2006.01)
(52) U.S. Cl.
CPC ............ *C12M 23/12* (2013.01); *C12M 25/06* (2013.01)

(58) Field of Classification Search
CPC ...... C12M 23/12; C12M 23/38; C12M 23/18; C12M 25/06; C12M 25/02
See application file for complete search history.

(56) References Cited

U.S. PATENT DOCUMENTS 5,232,838 A      8/1993  Nelson et al.
2005/0072030 A1* 4/2005  Wu ........................... G09F 3/02
                                                        40/324
(Continued)

FOREIGN PATENT DOCUMENTS

JP          2528174 B2 *  8/1996   ............ C12M 23/20
JP        2016106635 A    6/2016
(Continued)

OTHER PUBLICATIONS

Machine translation of JP2528174B2 (Year: 2025).*
International Search Report issued in PCT/KR2021/006668 dated Sep. 10, 2021, 5 pages.

*Primary Examiner* — Michael L Hobbs
(74) *Attorney, Agent, or Firm* — ROTHWELL, FIGG, ERNST & MANBECK, P.C.

(57)                    ABSTRACT

A cell culture device is provided. The cell culture device according to an exemplary embodiment of the present invention comprises: a body which includes a plurality of culture spaces formed therethrough in the height direction; and a plate-shaped cover member which is fixed to the bottom surface of the body while covering the open bottom portions of the culture spaces to thus form a culture surface where cells are cultured, and is surface-modified so as to allow the cells to be effectively attached to the culture surface.

8 Claims, 6 Drawing Sheets

(56) References Cited

U.S. PATENT DOCUMENTS

| | | | |
|---|---|---|---|
| 2005/0276728 A1* | 12/2005 | Muller-Cohn | ........ B01L 3/5085 |
| | | | 422/400 |
| 2013/0084624 A1 | 4/2013 | Waku | |
| 2014/0057346 A1 | 2/2014 | Johnson | |
| 2017/0175078 A1* | 6/2017 | Makino | .............. C08G 73/1028 |
| 2019/0338233 A1 | 11/2019 | Seo | |
| 2022/0002654 A1 | 1/2022 | Jang | |

FOREIGN PATENT DOCUMENTS

| | | | |
|---|---|---|---|
| KR | 20170140785 A | 12/2017 | |
| KR | 20170142729 A | 12/2017 | |
| KR | 20200056331 A | 5/2020 | |
| WO | 2011/093342 A1 | 8/2011 | |
| WO | 2018/042532 A1 | 3/2018 | |

* cited by examiner

100

CELL CULTURE DEVICE

CROSS REFERENCE TO RELATED APPLICATION

This application is a 35 U.S.C. 371 National Phase Entry Application from PCT/KR2021/006668 filed May 28, 2021, which claims priority to and the benefit of Korean Patent Application No. 10-2020-0068450, filed on Jun. 5, 2020, the disclosures of which are incorporated herein by reference in their entirety.

TECHNICAL FIELD

The present invention relates to a cell culture device.

BACKGROUND ART

Cell culture is a method used to culture or grow cells by removing a piece of tissue slice from a multicellular organism and supplying nutrients to the removed piece of tissue in a vessel.

Animal cells derived from human or animal tissue may be cultured in a state in which the cells are suspended in a medium or attached to a support. Suspended cells may grow independently in a state in which the cells are suspended in a medium, but adherent cells may grow only in a state in which the cells are attached to a culture surface such as a support.

Accordingly, to culture adherent cells using a cell culture device, a culture surface of the cell culture device is surface-modified by injecting a coating solution into the cell culture device so that the adherent cells can be smoothly attached to a culture surface of the cell culture device. After the culture surface of the cell culture device coated with the coating solution is dried for a predetermined time, a washing operation of injecting a separate washing solution into the cell culture device to remove excess coating solution is performed.

As a result, an operation of culturing the adherent cells using a conventional cell culture device has a drawback in that it is very cumbersome because it involves a seeding operation of attaching the cells to the culture surface and an operation of surface-modifying and washing the culture surface.

DISCLOSURE

Technical Problem

The present invention is designed to solve the problems of the related art, and thus it is an object of the present invention to provide a cell culture device capable of facilitating a seeding operation of adherent cells while maintaining mass productivity.

Technical Solution

To solve the above problems, the present invention provides a cell culture device which includes a body including a plurality of culture spaces formed therethrough in a height direction; and a plate-like cover member fixed to a bottom surface of the body to cover open bottom portions of the culture spaces in order to form a culture surface on which cells are cultured and surface-modified to facilitate smooth attachment of the cells to the culture surface.

As one example, the cover member may include a motif-coated plate-like nanofiber membrane, and a supporting member attached to one surface of the nanofiber membrane through an adhesive layer to support the nanofiber membrane, and an exposed surface of the nanofiber membrane may form the culture surface.

In this case, the nanofiber membrane may include a plurality of cutout portions cut at positions corresponding to the lower rims of the plurality of culture spaces, respectively, so that one surface of the supporting member can be exposed to the outside.

As another example, the cover member may be a plasma-treated plate-like film member, and one surface of the film member may form the culture surface.

Also, the body may include at least one welding protrusion protruding outward from a bottom surface to a certain height to surround the lower rims of the culture spaces.

In addition, the cover member may further include a release film laminated on one surface thereof. In this case, the release film may be removed after the surface modification of the cover member is completed.

Additionally, the plurality of culture spaces may be formed on the body to form a gap between two neighboring culture spaces.

Also, the cover member may be made of a non-toxic material.

Further, the plurality of culture spaces may be formed in the body so that the plurality of culture spaces are arranged in an m×n matrix structure in width and longitudinal directions of the body, and a display portion may be provided at an upper edge of the body to identify a location of each of the culture spaces.

Advantageous Effects

A cell culture device according to the present invention can reduce the unit cost of production by facilitating a seeding operation of adherent cells while maintaining mass productivity, and enhance operation convenience in cell culture.

MODES OF THE INVENTION

Figure 1:
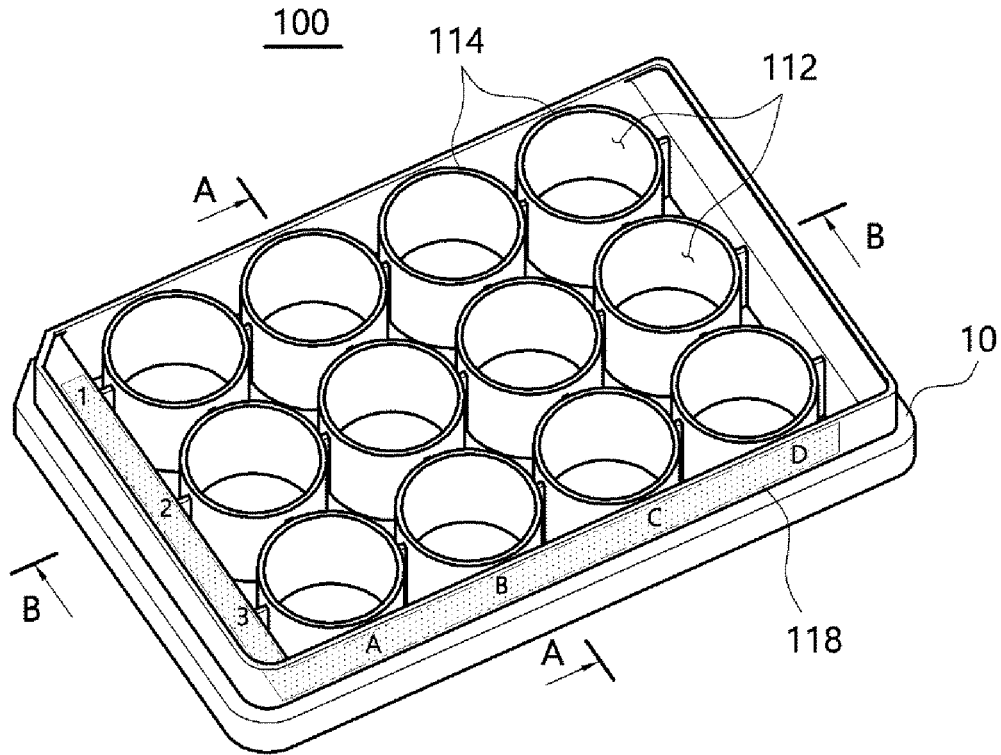
FIG. 1 is a diagram showing a cell culture device according to one embodiment of the present invention.
Figure 2:
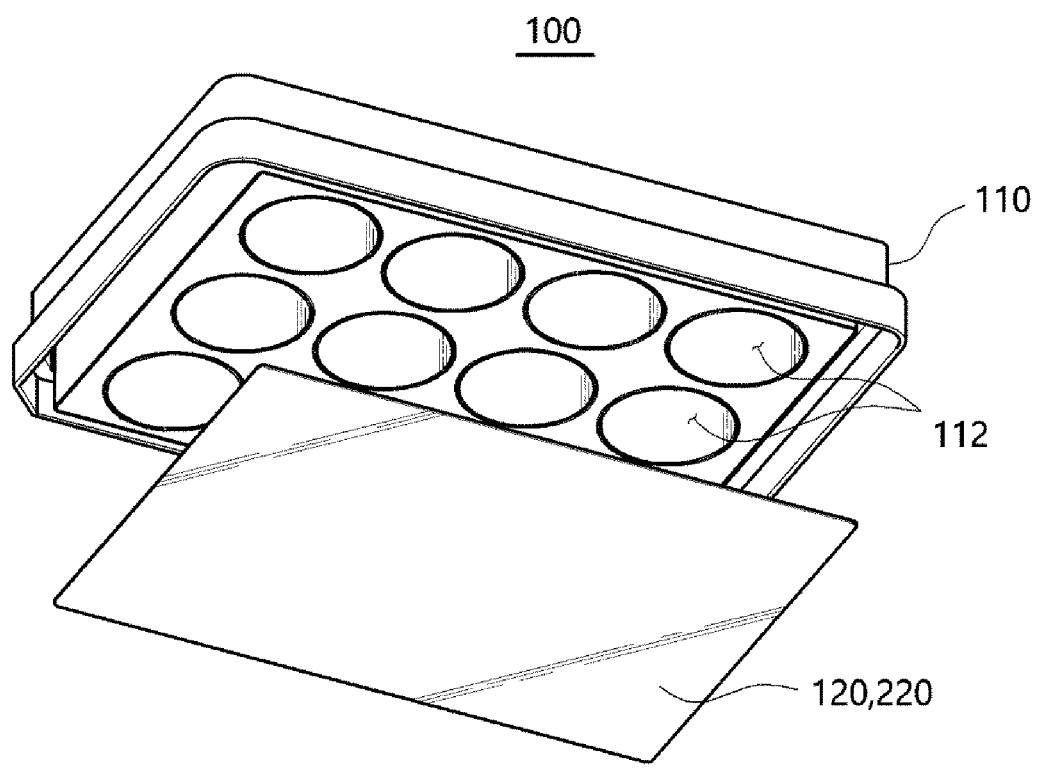
FIG. 2 is a diagram of the cell culture device shown in FIG. 1, which is viewed in a different direction in a state in which a cover member is separated from a body.

Hereinafter, the embodiments of the present invention will be described in detail with reference to the accompanying drawings to be easily implemented by those having ordinary skill in the art to which the present invention pertains. However, it should be understood that the present invention may be embodied in various different forms, and is not construed as limited to the embodiments set forth herein. In order to clearly describe the present invention, parts not related to the description are omitted, and like parts are denoted by like reference numerals throughout the specification.

A cell culture device 100 according to one embodiment of the present invention includes a body 110 and a cover member 120 or 220, as shown in FIGS. 1 to 4.

The body 110 may provide a culture space 112 for culturing cells. Such a body 110 may provide a plurality of culture spaces 112 to culture a plurality of cells in one culture process at the same time.

That is, the body 110 may include a plurality of culture spaces 112 formed therethrough in a height direction, and the plurality of culture spaces 112 may be formed in the body 110 so that the plurality of culture spaces 112 are arranged in an m×n matrix structure (wherein m and n are natural numbers) in width and longitudinal directions of the body 110.

Figure 3:
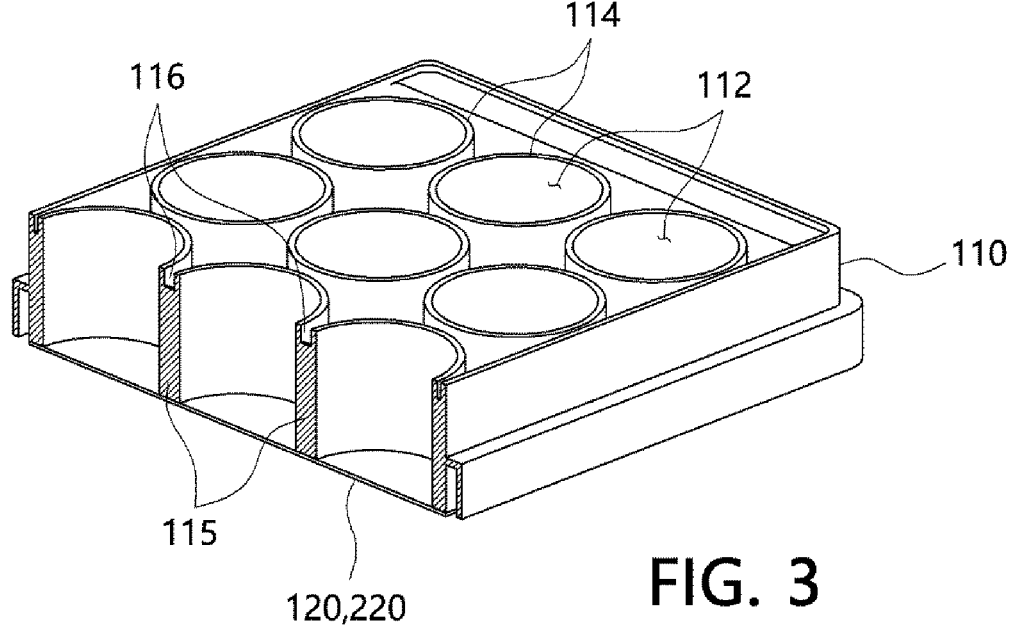
FIG. 3 is a cross-sectional diagram taken along the line A-A in FIG. 1.
Figure 4:
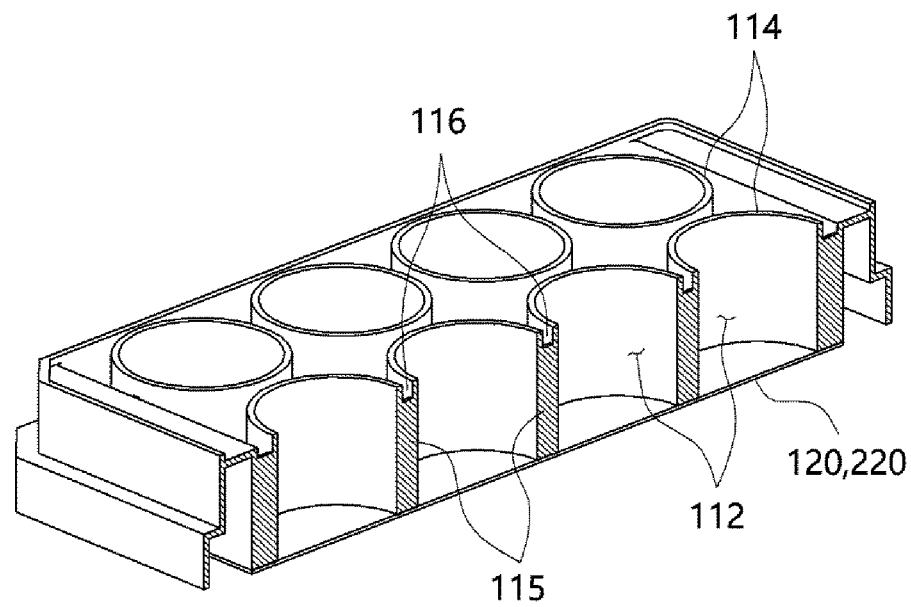
FIG. 4 is a cross-sectional diagram taken along the line B-B in FIG. 1.

As one example, the body 110 may include a plurality of compartment walls 114 extending from a bottom surface to a certain height and formed in a hollow shape, as shown in FIGS. 3 and 4.

Herein, each of the compartment walls 114 formed in a hollow shape may have open top portion and bottom portion. Accordingly, each of the compartment walls 114 may define a culture space 112 with open top portion and bottom portion.

In this way, the body 110 may form a plurality of culture spaces 112 partitioned by the plurality of compartment walls 114, and a medium for cell culture and cells to be cultured may be separately disposed in the plurality of culture spaces 112.

In this case, as shown in FIG. 1, a display portion 118 may be provided at an upper edge of the body 110 to identify a location of each of the culture spaces 112.

Accordingly, an operator may easily identify the location of each of the culture spaces 112 even when the plurality of culture spaces 112 are formed on the body 110.

Meanwhile, each of the compartment walls 114 defining the culture spaces 112 may be integrally connected to lateral portions of different neighboring compartment walls 114 through a connecting portion 115.

As one example, the body 110 may have the plurality of compartment walls 114 formed through insert injection molding, and the plurality of culture spaces 112 may be defined by the plurality of compartment walls 114.

As a result, the cell culture device 100 according to one embodiment of the present invention may secure mass productivity and reduce the unit cost of production because the body 110 may be produced through insert injection molding.

In this case, the plurality of culture spaces 112 may be formed in the body 110 to form a gap between two neighboring culture spaces 112.

That is, two compartment walls 114 defining two neighboring culture spaces 112 respectively may have upper rims spaced apart at a predetermined distance from each other.

For this purpose, the connecting portion 115 configured to connect two neighboring compartment walls 114 to each other may be formed to have a lower height than the compartment walls 114.

Accordingly, an inwardly recessed groove 116 may be formed at an upper end of the connecting portion 115, and two neighboring compartment walls 114 may be spaced apart at a predetermined distance in a state in which the upper rims of two neighboring compartment walls 114 are not connected to each other through the groove 116.

As a result, even when the medium containing the cells flows out through the open top portions of the culture spaces 112 while a medium containing the cells is injected toward each of the culture spaces 112 or the body 110 is transferred to other sites in a state in which each of the culture spaces 112 is filled with the medium, the medium flowing out through the open top portions of the culture spaces 112 may be blocked from flowing toward the neighboring culture spaces 112.

The cover member 120 or 220 may be fixed to the bottom surface of the body 110 to cover the open bottom portions of the culture spaces 112.

For this purpose, the cover member 120 or 220 may be provided as a plate-like member having a predetermined area, and may be fixed to the bottom surface of the body 110 to cover all the open bottom portions of the plurality of culture spaces 112.

As one example, the cover member 120 or 220 may be bonded to the bottom surface of the body 110 through welding using ultrasonic waves, heat, high-frequency waves, and the like.

Figure 5:
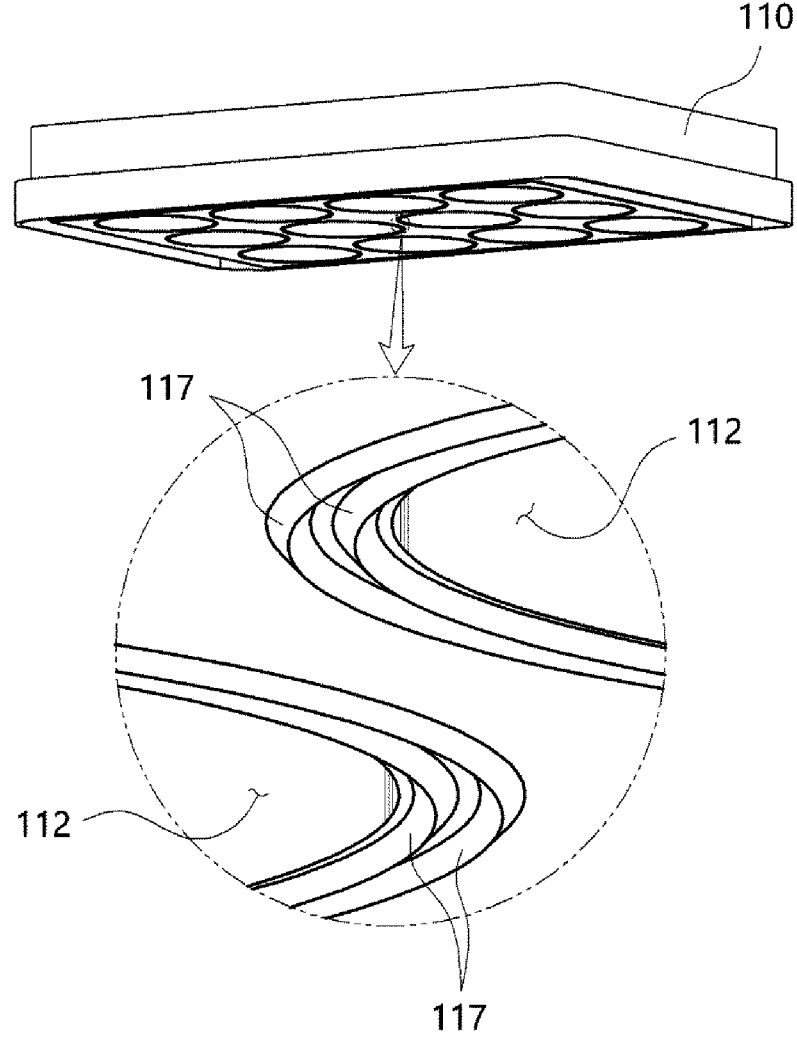
FIG. 5 is a diagram showing a welding protrusion formed on the body in the cell culture device according to one embodiment of the present invention.

In this case, the body 110 may include at least one welding protrusion 117 protruding outward from a bottom surface to a certain height to surround the lower rims of the culture spaces 112, as shown in FIG. 5.

That is, the at least one welding protrusion 117 may be melted when the body 110 and the cover member 120 or 220 are fused, so that the open bottom portions of the culture spaces 112 may be sealed while increasing the bonding force between the body 110 and the cover member 120 or 220.

However, a method of fixing the cover member 120 or 220 to the body 110 is not limited to the welding method. In this case, the cover member 120 or 220 may be attached to the bottom surface of the body 110 through an adhesive layer. Also, a method capable of hermetically sealing the open bottom portions of the culture spaces 112 while fixing the cover member 120 or 220 to the body 110 may be carried out using various methods known in the art.

Meanwhile, the cover member 120 or 220 may cover the open bottom portions of the culture spaces 112 as described above, and one surface of the cover member 120 or 220 covering the open bottom portions of the culture spaces 112 may form a culture surface. The cover member 120 or 220 may be surface-modified so that the cells may be smoothly attached to a portion of the cover member 120 or 220 forming the culture surface.

That is, in the cell culture device 100 according to one embodiment of the present invention, when the cover member 120 or 220 configured to cover the open bottom portions of the culture spaces 112 to form a culture surface is fixed to the bottom surface of the body 110 in a state in which the cover member 120 or 220 is surface-modified, the cells to be cultured may be smoothly attached to one surface (i.e., a culture surface) of the cover member 120 or 220 during a seeding operation.

In this way, when a medium containing cells to be cultured is injected into the culture spaces 112 during cell culture using the cell culture device 100 according to one embodiment of the present invention, the cells included in the medium may be smoothly attached to one surface of the cover member 120 or 220 forming a culture surface. Accordingly, a series of operations such as coating, drying, and washing for smoothly attaching the cells to the culture surface as known in the related art may be omitted.

As a result, a seeding operation for attaching the cells to the culture surface during the cell culture using the cell culture device 100 according to one embodiment of the present invention may be performed very easily, thereby enhancing the operator's convenience.

In addition, when a preparative operation for seeding the cells to be cultured is fully completed while attaching a plate-like cover member 120 or 220 to the bottom surface of the body 110 in a state in which the surface modification of the plate-like cover member 120 or 220 having a predetermined area is completed, mass productivity may be maintained while enhancing the operator's convenience.

Herein, the cover member 120 or 220 may be formed of a non-toxic material to smoothly culture the cells attached through the seeding operation.

Figure 6:
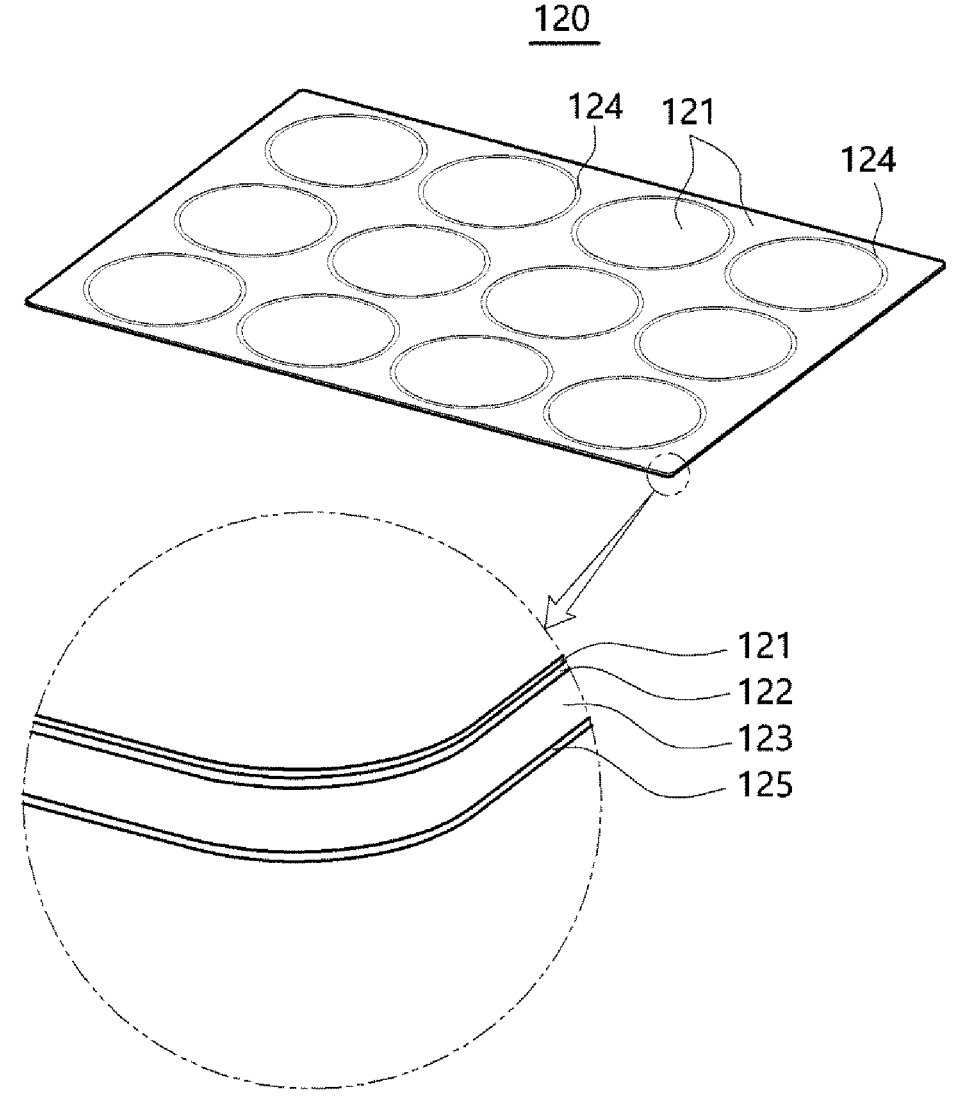
FIG. 6 is a diagram showing one example of the cover member applicable to the cell culture device according to one embodiment of the present invention.

As one example, the cover member 120 may include a motif-coated plate-like nanofiber membrane 121, and a supporting member 123 attached to one surface of the nanofiber membrane 121 through an adhesive layer 122 to support the nanofiber membrane 121, as shown in FIG. 6.

In this case, the cover member 120 may be fixed to the bottom surface of the body 110 so that the nanofiber membrane 121 covers the open bottom portions of the culture spaces 112, and one surface of the nanofiber membrane 121 exposed to each of the culture spaces 112 may form a culture surface to which the cells to be cultured are attached.

Accordingly, the cells to be cultured may be smoothly attached to one surface of the nanofiber membrane 121, and the cells attached to one surface of the nanofiber membrane 121 may be cultured with nutrients supplied from the medium filled in the culture spaces 112.

In this case, the nanofiber membrane 121 may include a plurality of cutout portions 124 formed at positions corresponding to the lower rims of the plurality of culture spaces 112, respectively, so that one surface of the supporting member 123 can be exposed to the outside.

As one example, the cutout portions 124 may be formed at positions corresponding to the lower rims of the compartment walls 114, and a nanofiber membrane 121 having a smaller area than a cross-sectional area of each of the culture spaces 112 may be disposed inside each of the cutout portions 124.

In this way, in a case in which the cover member 120 is attached to the bottom surface of the body 110, the supporting member 123 may come into direct contact with the bottom surface of the body 110 through the cutout portions 124, and the entire area of the nanofiber membrane 121 disposed inside each of the cutout portions 124 may be completely accommodated in each of the culture spaces 112.

That is, at least one welding protrusion 117 formed on the bottom surface of the body 110 may come into direct contact with the supporting member 123 through the cutout portions 124.

As a result, the bonding force between the cover member 120 and the body 110 may be enhanced, and the leakage of the medium filled in the culture spaces 112 to the outside of the culture spaces 112 by moving along the nanofiber membrane 121 may be fundamentally blocked.

Figure 7:
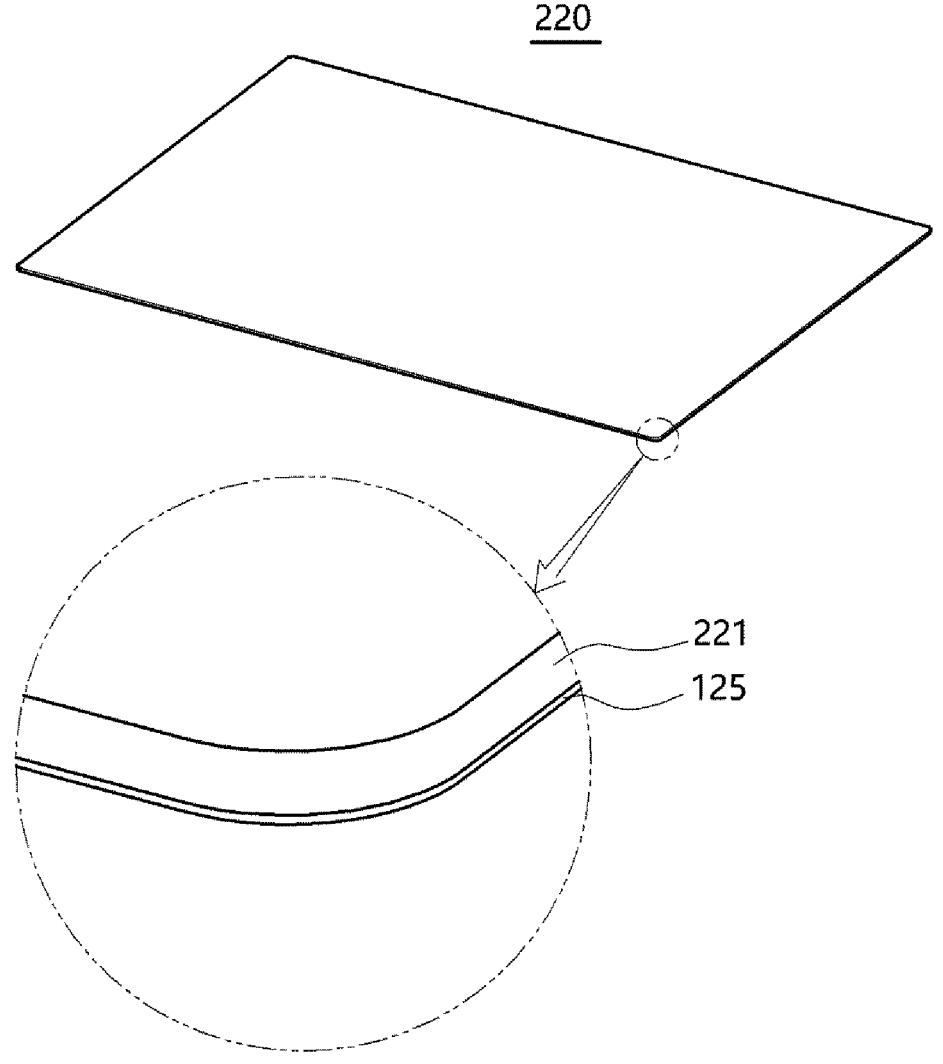
FIG. 7 is a diagram showing another example of the cover member applicable to the cell culture device according to one embodiment of the present invention.

As another example, the cover member 220 may be a plasma-treated plate-like film member 221, as shown in FIG. 7.

Accordingly, the cells to be cultured may be smoothly attached to a surface of the film member 221, and the cells attached to the surface of the film member 221 may be cultured with nutrients supplied from the medium filled in the culture spaces 112.

However, the type of the cover member 120 or 220 is not limited thereto, and various materials used for cell culture as known in the art may be used as long as the materials are implemented in a plate-like shape and the cells are easily attached to the materials.

Meanwhile, the cover member 120 or 220 may further include a release film 125 laminated on one surface thereof.

Such a release film 125 may remain attached to one surface of the cover member 120 or 220 during the surface modification of the cover member 120 or 220, and may be removed from one surface of the cover member 120 or 220 after the surface modification is completed.

That is, the release film 125 may be attached to one surface of the supporting member 123 or one surface of the film member 221 as described above.

Such a release film 125 may cover a surface of the cover member 120 or 220 other than the culture surface to which the cells are attached in a process of surface-modifying the nanofiber membrane 121 or the film member 221.

As a result, it is possible to prevent surface modification of an unnecessary region in the cover member 120 or 220 or that a washing solution used in a process of washing a coating solution may be smeared on one surface of the supporting member 123 in advance.

While one embodiment of the present invention has been described above, the spirit of the present invention is not limited to the embodiments proposed in this specification. Other embodiments may be easily suggested by adding, changing and removing components by those skilled in the art and will fall within the spirit and scope of the present invention.

The invention claimed is:

1. A cell culture device comprising:
   a body including a plurality of culture spaces formed therethrough in a height direction;
   a plate-like cover member fixed to a bottom surface of the body and covering open bottom portions of the culture spaces in order to form a culture surface configured for culturing cells thereon, wherein the plate-like cover member is surface-modified to facilitate smooth attachment of the cells to the culture surface; and
   a release film laminated on a surface of the plate-like cover member opposite to the culture surface,
   wherein the plate-like cover member is fixed to the body in a state in which surface modification of the plate-like cover member is completed, and
   wherein the release film is configured to remain attached to the plate-like cover member during the surface modification of the plate-like cover member and is configured to be removable from the plate-like cover member after the surface modification is completed.

2. The cell culture device of claim 1, wherein the cover member comprises a motif-coated plate-like nanofiber membrane, and a supporting member attached to one surface of the nanofiber membrane through an adhesive layer to support the nanofiber membrane,
   and wherein the culture surface is an exposed surface of the nanofiber membrane.

3. The cell culture device of claim 2, wherein the nanofiber membrane comprises a plurality of cutout portions cut at positions corresponding to lower rims of the plurality of culture spaces, respectively, so that one surface of the supporting member is configured to be exposed to the outside.

4. The cell culture device of claim 1, wherein the cover member is a plasma-treated plate-like film member, and one surface of the film member forms the culture surface.

5. The cell culture device of claim 1, wherein the body comprises at least one welding protrusion protruding outward from a bottom surface to a certain height to surround lower rims of the plurality of culture spaces.

6. The cell culture device of claim 1, wherein the plurality of culture spaces are formed in the body to form a gap between two neighboring culture spaces.

7. The cell culture device of claim 1, wherein the cover member is made of a non-toxic material.

8. The cell culture device of claim 1, wherein the plurality of culture spaces are formed in the body so that the plurality of culture spaces are arranged in an m×n matrix structure in width and longitudinal directions of the body, and a display portion is provided at an upper edge of the body to identify a location of each of the culture spaces.

* * * * *